United States Patent
Minami et al.

(10) Patent No.: US 9,308,216 B2
(45) Date of Patent: Apr. 12, 2016

(54) RUTIN-RICH EXTRACT AND METHOD OF MAKING SAME

(71) Applicant: ALPS Pharmaceuticals, IND. Co., Ltd., Gifu (JP)

(72) Inventors: Kazunobu Minami, Gifu (JP); Shinji Taniwaki, Gifu (JP); Akiko Katsumata, Gifu (JP)

(73) Assignee: Alps Pharmaceuticals Ind. Co., Ltd., Gifu (JP)

( * ) Notice: Subject to any disclaimer, the term of this patent is extended or adjusted under 35 U.S.C. 154(b) by 0 days.

(21) Appl. No.: 14/389,573

(22) PCT Filed: Oct. 22, 2012

(86) PCT No.: PCT/JP2012/006758
§ 371 (c)(1),
(2) Date: Sep. 30, 2014

(87) PCT Pub. No.: WO2014/064731
PCT Pub. Date: May 1, 2014

(65) Prior Publication Data
US 2015/0157654 A1    Jun. 11, 2015

(51) Int. Cl.
| | | |
|---|---|---|
| A61K 36/00 | (2006.01) |
| A61K 31/7048 | (2006.01) |
| C07H 17/07 | (2006.01) |
| A23L 1/30 | (2006.01) |
| A61K 36/74 | (2006.01) |
| A61K 36/18 | (2006.01) |

(52) U.S. Cl.
CPC ............ *A61K 31/7048* (2013.01); *A23L 1/3002* (2013.01); *A61K 36/74* (2013.01); *C07H 17/07* (2013.01); *A23V 2002/00* (2013.01); *A61K 36/18* (2013.01)

(58) Field of Classification Search
None
See application file for complete search history.

(56) References Cited

U.S. PATENT DOCUMENTS 2,534,275 A    12/1950    Krewson et al.

FOREIGN PATENT DOCUMENTS

| WO | WO-03/092410 A1 | 11/2003 |
| WO | WO-2004/027074 A2 | 4/2004 |
| WO | WO-2006/070883 A1 | 7/2006 |
| WO | WO-2007/109802 A2 | 9/2007 |

OTHER PUBLICATIONS

Law et al, Dual-wavelength absorbance ratio and spectrum scanning techniques for identification of flavonoids by high-performance liquid chromatography. Journal of Chromatography (1987), vol. 388, No. 1, pp. 225-233.*
Balz, et al., "Uncaria elliptica a major source of rutin", Planta Medica, 1979, vol. 36, No. 2, pp. 174-177.
Gulpinar, et al., "Estimation of in vitro neuroprotective properties and quantification of rutin and fatty acids in buckwheat (Fagopyrum esculentum Moench) cultivated in Turkey", Food Research International, May 2002, vol. 46, No. 2, pp. 536-543.
Legnerova, et al., "Using on-line solid phase extraction for simultaneous determination of ascorbic acid and rutin trihydrate by sequential injection analysis". Analytica Chimica Acta, 2003, vol. 497, No. 1-2, pp. 165-174.
Martins, et al., "Antioxidant effect of Stryphnodendron rotundifolium martius extracts from Cariri-Ceara state (Brazil): potential involvement in its therapeutic use", Molecules, Jan. 18, 2012, vol. 17, pp. 934-950.
Wu, et al., "Determination of flavonoids and ascorbic acid in grapefruit peel and juice by capillary electrophoresis with electrochemical detection", Food Chemistry, 2007, vol. 100, No. 4, pp. 1573-1579.

* cited by examiner

*Primary Examiner* — Qiuwen Mi
(74) *Attorney, Agent, or Firm* — Cesari and McKenna LLP

(57) ABSTRACT

A method of obtaining a rutin-rich extract from a plant and a rutin-rich extract of *Uncaria elliptica* thus obtained.

18 Claims, No Drawings

RUTIN-RICH EXTRACT AND METHOD OF MAKING SAME

CROSS REFERENCE TO RELATED APPLICATIONS

This application is the National Stage of International Application No. PCT/JP2012/006758, filed on Oct. 22, 2012, the content of which is hereby incorporated by reference in its entirety.

TECHNICAL FIELD

This invention relates to a rutin-rich extract and to a method of making the rutin-rich extract.

BACKGROUND ART

Rutin is a natural flavonoid used as a starting material of Troxerutin, which increases endurance of capillaries and lowers permeability of the venous blood vessel walls. A clinical study showed that treating patients with a rutin derivative, Venoruton, led to improvement of post thrombotic syndrome. See, Panminerva Medicine, 53, page 13, 2011. Another study found that rutin is one of the most effective anti-thrombosis agents. See, The Journal of Clinical Investigation, 122, No 6, 2012. Rutin as a starting material for pharmaceutical agents is becoming more important.

To extract and purify rutin from various plant sources, e.g., Sophora Japonica (Asia), Fava d'anta (Brazil), and Uncaria elliptica (Brazil), water and methanol solvents are typically used. Practically, however, rutin-rich extracts derived from such plant sources have significant disadvantages, such as being a dense brown color and containing a higher iron content in comparison with rutin-rich extracts from other sources. This brown color is attributed to pigments in the plant.

SUMMARY OF INVENTION

It is very difficult to eliminate this brown color and reduce iron content by conventional extraction and/or purification methods, as iron appears to be tightly incorporated into the pigments. Attempts have been made to overcome these disadvantages. However, these attempts failed to reduce iron incorporated in pigments and at the same time maintain good rutin yield.

There is a need for an economical procedure suitable for large-scale applications that can produce rutin-rich extracts with high rutin content, low iron content, and reduced pigmentation.

This invention is based on the unexpected discovery of particular combinations of alcohols and acids that can be used to obtain rutin-rich extracts from plants that are low in iron content and pigmentation.

Accordingly, described herein is a method of obtaining a rutin-rich extract from a plant. The method includes dissolving a rutin-containing plant extract in methanol or ethanol to obtain a crude rutin extract solution, the solid rutin-containing plant extract containing 90% to 95% rutin by weight and 100 to 300 ppm iron; reducing the volume of the crude rutin extract solution to obtain a concentrate; obtaining a mixture by adding to the concentrate an acid at 1-15% by weight of the rutin-containing plant extract, and optionally a C1-C4 alcohol, water, or both, wherein the rutin-containing plant extract constitutes 8% to 30% (w/v) of the mixture and the acid is selected from the group consisting of ascorbic acid, citric acid, tartaric acid, gallic acid, and malic acid; allowing the mixture to stand for formation of a precipitate; and isolating the precipitate, thereby obtaining a rutin-rich extract that contains less than 20 ppm iron.

The rutin-containing plant extract can be obtained as a crude precipitate from extracting Uncaria elliptica, Sophora Japonica, or Fava d'anta with water, an alcohol, or an aqueous alcohol.

In some embodiments, the acid is added at 1-10%, e.g., 1-5%, or 2-4%, by weight of the rutin-containing plant extract. In cases where water and the C1-C4 alcohol are added, the ratio of water to the C1-C4 alcohol can be 1:1 to 5:1, e.g., 1:1 to 3:1. Water and the C1-C4 alcohol can be added separately, at the same time, or in the form of an aqueous C1-C4 alcohol.

Also featured herein is a rutin-rich extract of Uncaria elliptica, the extract containing 97% to 99% rutin as measured by HPLC and less than 20 ppm of iron, the absorption of the extract at 550 nm being lower than 0.2. The extract can also contain 5% to 10% water by weight. It can be prepared by the above-described method.

DESCRIPTION OF EMBODIMENTS

The details of one or more embodiments of the invention are set forth in the description below. Other features, objects, and advantages of the invention will be apparent from the description and from the claims.

Described herein is a method for obtaining rutin-rich extracts from plant sources using novel combinations of alcohols and acids. Rutin-rich extracts obtained by the method have significantly reduced pigmentation and iron content as compared to extracts prepared by conventional methods.

Using conventional methods known in the art, a solid rutin-containing extract can be prepared from various plant sources, e.g., Sophora Japonica (Asia), Fava d'anta (Brazil), and Uncaria elliptica (Brazil). Such methods include, but are not limited to, soaking, heating, shaking, stirring, or infusing plant material, e.g., stems and leaves, in various solvents. The plant material used can be in the form of whole dried plant, crushed plant, or powder. The solvents include water, alcohols (e.g., methanol), or aqueous alcohols. After extraction, the extract solution can be separated from the solid by sieving, filtering, pressing, or other suitable techniques. The filtrate can be concentrated and cooled to allow precipitate to form, thus obtaining a solid rutin-containing extract. For descriptions of various extraction methods, see, e.g., Chinese Patent 1013579; US2006/0099690; and Dighe et al., International Journal of Pharma and Bio Sciences, 2(1):750-757 (2011).

Typically, solid rutin-containing extracts prepared by these methods have high iron content, e.g., 100-300 ppm, and are heavily pigmented, e.g., yellow or brown, particularly in extracts originating from Uncaria elliptica. Rutin can constitute 85% to 90% by weight of these solid rutin-containing extracts.

A solid rutin-containing extract thus prepared can be dissolved in an alcohol solvent, preferably methanol or ethanol, to obtain a crude rutin extract solution. For example, 0.05-0.13 g of the solid extract can be dissolved per 1 ml of the solvent. The crude extract solution can be further concentrated, e.g., under atmospheric pressure, to reduce its volume, e.g., by 4 to 10 fold. The final volume of the crude extract solution can be predetermined based on the desired volume and contents of the mixture described below.

An acid, and optionally a C1-C4 alcohol, e.g., methanol, ethanol, propanol, or n-butanol, are added to the above-described crude rutin extract solution to obtain a mixture. Water can also be included in the mixture.

The acid used is selected from ascorbic acid, citric acid, tartaric acid, gallic acid, and malic acid. It is added to the crude rutin extract solution at about 1-15%, e.g., 1-10%, or 1-5%, by weight of the above-described solid rutin-containing extract used to prepare the crude rutin extract solution.

The mixture must contain at least one C1-C4 alcohol. For example, as described above, methanol or ethanol (i.e., a C1-C4 alcohol) can be used to make the crude rutin extract solution from the solid rutin-containing extract. It may not be necessary to add additional C1-C4 alcohol to the crude rutin extract solution. In some cases, in order to obtain a mixture containing 8% to 30% (w/v) solid rutin-containing extract, a C1-C4 alcohol, an aqueous C1-C4 alcohol, or a C1-C4 alcohol and water can be added, e.g., at 2-12 fold (v/w) of the solid rutin-containing extract. The additional C1-C4 alcohol added can be the same or different from the alcohol used to make the crude rutin extract solution.

Rutin exists as various hydrates, such as monohydrate, dihydrates, and trihydrate. It is known that anhydrate and monohydrate are unstable. Therefore, it is preferable to prepare relatively stable dihydrate or trihydrate by aquation with water during the purification process. Accordingly, water can be added to the crude rutin extract solution. It can be added separately. It can also be added in the form of an aqueous C1-4 alcohol. The ratio of water to the C1-C4 alcohol can be 1:1 to 5:1, e.g., 1:1 to 3:1. As noted above, the final mixture preferably contains 8% to 30% (w/v) solid rutin-containing extract.

The mixture containing the crude rutin extract solution, the C1-C4 alcohol, the acid, and optional water is then allowed to stand for precipitate, e.g., crystal, to form. For example, the mixture can be further concentrated, and the concentrated mixture is stirred and allowed to cool for precipitate to form. The precipitate can be collected by any suitable technique, e.g., filtration, rinsed with an alcohol and/or water, and dried.

The precipitate, i.e., a rutin-rich extract, can contain 97% to 99% rutin as measured by HPLC, and less than 20 ppm of iron, i.e., less than 10 ppm. It also has low pigmentation, e.g., the absorption of the extract at 550 nm being lower than 0.2. It can also include 5% to 10% water by weight. The rutin-rich extract can have any particle size, e.g., 5 um (micrometer) or less. For example, it can have nano-sized particles.

The rutin-rich extract prepared by the method described above is useful for various applications. It can be formulate as a pharmaceutical composition, e.g., a drug. It can also be used as a nutritional supplement or food additive.

EXAMPLES

The specific examples below are to be construed as merely illustrative, and not limitative of the remainder of the disclosure in any way whatsoever. Without further elaboration, it is believed that one skilled in the art can, based on the description herein, utilize the present invention to its fullest extent. All publications cited herein are hereby incorporated by reference in their entirety.

Values of iron content, purity and absorbance described in EXAMPLES 1-4 below were obtained by the following procedures:

(1) Iron Content 1.0 g of sample was accurately obtained and vitriolized. 2 ml of hydrochloric acid was added to the residue. The sample was then dried, and heated in boiling water after addition of 10 ml of water with one drop of hydrochloric acid. After cooling, the volume was accurately adjust to 10.0 ml and then filtered through a 0.45 micron filter. The concentration of iron in the sample solution was determined by ICP analysis.

(2) Visible Absorption 1.0 g of sample was dissolve in 15 ml of dimethylformamide (DMF). After adjusting the volume to 20.0 ml with DMF, the solution was filtered through a 0.45 micron filter. The absorption of the filtered sample was measured at 550 nm with a path length of 1.0 cm.

(3) HPLC Analysis

HPLC analysis was performed in accordance with EP monograph Rutoside trihydrate, related substances by liquid chromatography. Briefly, the reagents and conditions used are set forth below:

[Chem. 1]
Test solution: Dissolve 0.10 g of substance to be examined in 20 ml of methanol and dilute to 100.0 ml with mobile phase B.

Reference solution (a): Dissolve 10.0 mg of rutoside trihydrate CRS in 10.0 ml of methanol.

Reference solution (b): Dilute 1.0 ml of reference solution (a) to 50.0 ml with mobile phase B.

Column (LiChrospher 100 RP-8, C8, 4.0×250 mm, Agilent):
 size: 1=0.25 m, i.d.=4.0 mm,
 stationary phase: octylsilyl silica gel for chromatography (5 μm)
 temperature: 30° C.
Mobile phase:
 mobile phase A: mix 5 volumes of tetrahydrofuran with 95 volume of a 15.6 g/l solution of sodium dihydrogen phosphate adjusted to pH 3.0 with phosphoric acid.
 mobile phase B: mix 40 volumes of tetrahydrofuran with 60 volume of a 15.6 g/l solution of sodium dihydrogen phosphate adjusted to pH 3.0 with phosphoric acid.

| [Chem.2] Gradient timetable | | |
|---|---|---|
| Time (min) | Mobile phase A (%) | Mobile phase B (%) |
| 0-10 | 50-0 | 50-100 |
| 10-20 | 0 | 100 |
| 20-21 | 0-50 | 100-50 |
| 21-25 | 50 | 50 |

Flow rate: 1 ml/min.
Detection: spectrophotometer at 280 nm.
Injection: 20 μl.

The acids and alcohols used in Examples 1-4 below were obtained from Wako Pure Chemical Industries, Ltd (Osaka): ascorbic acid (minimum 99.5% first grade); citric acid (minimum 98.0% special grade); malic acid (minimum 99.0% special grade); gallic acid (98.0-103.0% first grade); tartaric acid (minimum 99.0% first grade); methanol (minimum 99.5% first grade); ethanol (minimum 99.5% special grade); n-propanol (minimum 99.7% special grade); n-butanol (minimum 99.0% special grade).

Example 1

Preparation of a Crude Rutin Extract Solution

*Uncaria eliptica* stems and leaves were extracted with water and/or alcohol using conventional procedures to obtain solid rutin-containing extracts. Three sets of solid rutin-containing extract (50 g each) were dissolved in 600 ml of methanol and stirred for two hours at 30-35 degrees C. (Celsius). Each solution was filtered and concentrated under atmospheric pressure to produce 300 ml of crude rutin extract solution.

The solid rutin-containing extracts thus prepared contained 85-90% (w/w) rutin and 100-200 ppm iron. It developed a dark brown color when dissolved in organic solvents and the average absorbance in DMF at 550 nm was 0.8-1.3.

The data are summarized in Table 1 below.

TABLE 1

| Lot No. | Iron (ppm) | Absorption (550 nm) | Rutin content (%), wt/wt | Water content (%) |
|---|---|---|---|---|
| A | 167 | 1.173 | 88.0 | 9.6 |
| B | 174 | 1.149 | 89.2 | 9.2 |
| C | 160 | 1.048 | 88.6 | 8.9 |

Example 2

Influence of Ascorbic Acid in Combination with Various Solvents (1) Methanol

Three sets of crude rutin extract solution, each obtained from dissolving 50 g of solid rutin-containing extract in 600 ml methanol (MeOH), were concentrated under atmospheric pressure to give 300 ml of volume. The concentrates each received 0, 1.0, or 5.0 g of ascorbic acid and were each further concentrated to give a volume of 150 ml. After allowing crystallization by cooling, purified rutin crystal was collected by filtration followed by rinsing with methanol. The purified rutin was dried at 60 degrees C. (Celsius) for 5 hours, and analyzed as described above. The results are summarized in Table 2 below. Addition of ascorbic acid during the crystallization procedure reduced residual iron and decreased absorption at 550 nm in a dose dependent manner.

TABLE 2

| No. | Extraction | Crystallization | Acid | Amount (%)* | Iron (ppm) | Absorption (550 nm) | Rutin HPLC area (%) | Yield (%) | Water content (%) |
|---|---|---|---|---|---|---|---|---|---|
| 1 | MeOH | MeOH | none | — | 22.4 | 0.235 | 99.0 | 70.2 | 4.9 |
| 2 | MeOH | MeOH | Ascorbic acid | 2 | 13.7 | 0.146 | 98.9 | 69.9 | 4.7 |
| 3 | MeOH | MeOH | Ascorbic acid | 10 | 10.2 | 0.114 | 98.4 | 70.5 | 5.5 |

*Amount of additive relative to weight of solid rutin-containing extract (2) Ethanol Two sets of 500 ml crude rutin extract solution, obtained from dissolving 25 g of solid rutin-containing extract in ethanol (EtOH), were each concentrated under atmospheric pressure to give 100 ml of volume. The concentrates each received 25 ml of water that contained 0 or 0.5 g of ascorbic acid. After allowing crystallization by stirring and cooling, purified rutin crystal was collected by filtration, followed by rinsing with 15 ml of 95% ethanol. The purified rutin was dried at 60 degrees C. (Celsius) for 5 hours and analyzed as described above. The results are summarized in Table 3 below. The effects of ascorbic acid were not as significant as in the case when methanol was used in the crystallization process (see above).

TABLE 3

| No. | Extraction | Crystallization | Acid | Amount (%)* | Iron (ppm) | Absorption (550 nm) | Rutin HPLC area (%) | Yield (%) | Water content (%) |
|---|---|---|---|---|---|---|---|---|---|
| 4 | EtOH | Water/EtOH | none | — | 10.7 | 0.280 | 97.1 | 84.0 | 9.2 |
| 5 | EtOH | Water/EtOH | Ascorbic acid | 2 | 9.59 | 0.260 | 97.0 | 83.5 | 8.7 |

*Amount of additive relative to weight of solid rutin-containing extract (3) Propanol Two sets of crude rutin extract solutions were prepared by dissolving 25 g of solid rutin-containing extract in 300 ml MeOH. Each extract was concentrated under atmospheric pressure to give 43 ml of volume. The concentrates each received aqueous propanol (n-propanol:water=1:1; total 200 ml) that that contained 0 or 0.5 g of ascorbic acid. After allowing crystallization by stirring and cooling, purified rutin crystal was collected by filtration. The rutin crystal was rinsed with 25 ml of n-propanol followed by water. The purified rutin was dried at 80 degrees C. (Celsius) for 6 hours and analyzed. The analytical results are summarized in Table 4 below. Ascorbic acid reduced residual iron and decreased absorption at 550 nm of the purified rutin.

TABLE 4

| No. | Extraction | Crystallization | Acid | Amount (%)* | Iron (ppm) | Absorption (550 nm) | Rutin HPLC area (%) | Yield (%) | Water content (%) |
|---|---|---|---|---|---|---|---|---|---|
| 6 | MeOH | Water/propanol | none | — | 26.7 | 0.296 | 98.2 | 76.4 | 8.1 |
| 7 | MeOH | Water/propanol | Ascorbic acid | 2 | 12.8 | 0.148 | 98.2 | 74.8 | 8.1 |

*Amount of additive relative to weight of solid rutin-containing extract (4) Butanol Four crude rutin extract solutions were each prepared by dissolving 25 g of solid rutin-containing extract in 300 ml MeOH. Each extract solution was concentrated under atmospheric pressure to give 43 ml of volume. The concentrates each received aqueous n-butanol (water:n-butanol=133:67 ml) that contained 0, 0.25, 0.5, or 2.5 g of ascorbic acid. After allowing crystallization by stirring and cooling, purified rutin crystal was collected by filtration, and then rinsed with 25 ml of n-butanol followed with 100 ml of water. The purified rutin was dried at 80 degrees C. (Celsius) for 6 hours and analyzed as described above. The analytical results are summarized in Table 5. Ascorbic acid reduced residual iron and decreased absorption at 550 nm of the purified rutin.

TABLE 5

| No. | Extraction | Crystallization | Acid | Amount (%)* | Iron (ppm) | Absorption (550 nm) | Rutin HPLC area (%) | Yield (%) | Water content (%) |
|---|---|---|---|---|---|---|---|---|---|
| 15 | MeOH | Water/BuOH | none | — | 60.3 | 0.701 | 97.6 | 83.6 | 8.4 |
| 16 | MeOH | Water/BuOH | Ascorbic acid | 1 | 15.5 | 0.245 | 98.2 | 83.5 | 8.0 |
| 17 | MeOH | Water/BuOH | Ascorbic acid | 2 | 1.86 | 0.097 | 98.2 | 82.4 | 7.9 |
| 18 | MeOH | Water/BuOH | Ascorbic acid | 10 | 1.36 | 0.074 | 98.1 | 82.9 | 8.0 |

*Amount of additive relative to weight of solid rutin-containing extract

Example 3

Influence of Various Acids in Combination with Aqueous Butanol

Seven crude rutin extract solutions were each prepared by dissolving 25 g of solid rutin-containing extract, obtained as described in Example 1, in 300 ml MeOH. The extracts were concentrated under atmospheric pressure to give 43 ml of volume each. The concentrates each received aqueous butanol (water:n-butanol=133:67 ml) that contained tartaric acid, citric acid, malic acid, or gallic acid in the amount shown in Table 6 below.

After allowing crystallization of the concentrates by stirring and cooling, purified rutin crystal was collected by filtration. The purified rutin was rinsed with 25 ml of n-butanol followed with 100 ml of water. The purified rutin was dried at 80 degrees C. (Celsius) for 6 hours and analyzed as described above. The results are shown in Table 6. Except for gallic acid, all other acids reduced residual iron and decreased absorption at 550 nm of the purified rutin.

The results described in Examples 2 and 3 indicate that a combination of butanol and ascorbic acid is the most effective for reducing both iron content and yellow color showing absorption at 550 nm.

TABLE 6

| No. | Extraction | Crystallization | Acid | Amount (%)* | Iron (ppm) | Absorption (550 nm) | Rutin HPLC area (%) | Yield (%) | Water content (%) |
|---|---|---|---|---|---|---|---|---|---|
| 8 | MeOH | Water/BuOH | none | — | 60.3 | 0.701 | 97.6 | 83.4 | 8.4 |
| 9 | MeOH | Water/BuOH | Tartaric acid | 2 | 15.2 | 0.224 | 98.0 | 83.5 | 8.3 |
| 10 | MeOH | Water/BuOH | Citric acid | 2 | 27.6 | 0.313 | 98.1 | 80.8 | 8.0 |
| 11 | MeOH | Water/BuOH | Malic acid | 2 | 27.9 | 0.353 | 98.2 | 82.8 | 8.0 |
| 12 | MeOH | Water/BuOH | Gallic acid | 2 | 60.6 | 0.809 | 98.0 | 82.9 | 8.0 |
| 13 | MeOH | Water/BuOH | Tartaric acid | 10 | 10.8 | 0.101 | 97.4 | 81.2 | 7.2 |
| 14 | MeOH | Water/BuOH | Tartaric acid Citric acid Gallic acid | 3% each | 18.6 | 0.146 | 97.3 | 81.0 | 7.3 |

*Amount of additive relative to weight of solid rutin-containing extract

Example 4

Influence of Solvents

Purified rutin was obtained using various solvents without any acid. It was observed that aqueous butanol and aqueous ethanol gave better rutin yield as compared to other solvents. See Table 7 below.

TABLE 7

| No. | Extraction | Crystallization | Acid | Amount (%)* | Iron (ppm) | Absorption (550 nm) | Rutin HPLC area (%) | Yield (%) | Water content (%) |
|---|---|---|---|---|---|---|---|---|---|
| 1 | MeOH | MeOH | none | — | 22.4 | 0.235 | 99.0 | 70.2 | 4.9 |
| 4 | EtOH | Water/EtOH | none | — | 10.7 | 0.280 | 97.1 | 84.0 | 9.2 |
| 6 | MeOH | Water/propanol | none | — | 26.7 | 0.296 | 98.2 | 76.4 | 8.1 |
| 15 | MeOH | Water/BuOH | none | — | 60.3 | 0.701 | 97.6 | 83.6 | 8.4 |

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

The invention claimed is:

1. A method of obtaining a rutin-rich extract from a plant, the method comprising,
   dissolving a rutin-containing plant extract in methanol or ethanol to obtain a crude rutin extract solution, the rutin-containing plant extract containing 90% to 95% rutin by weight and 100 to 300 ppm iron;
   reducing the volume of the crude rutin extract solution to obtain a concentrate;
   obtaining a mixture by adding to the concentrate an acid at 1-15% by weight of the rutin-containing plant extract, and optionally a C1-C4 alcohol, water, or both, wherein the rutin-containing plant extract constitutes 8% to 30% (w/v) of the mixture and the acid is selected from the group consisting of ascorbic acid, citric acid, tartaric acid, gallic acid, and malic acid;
   allowing the mixture to stand for formation of a precipitate; and
   isolating the precipitate, thereby obtaining a rutin-rich extract that contains less than 20 ppm iron.

2. The method of claim 1, wherein the rutin-containing plant extract is obtained as a crude precipitate from extracting *Uncaria elliptica, Sophora Japonica,* or Fava d'anta with water, an alcohol, or an aqueous alcohol.

3. The method of claim 1, wherein the C1-C4 alcohol and water are added.

4. The method of claim 3, wherein the C1-C4 alcohol and water are added in the form of an aqueous C1-C4 alcohol that contains 5-80% water by volume.

5. The method of claim 3, wherein the ratio of water to the C1-C4 alcohol is 1:1 to 5:1 by volume.

6. The method of claim 5, wherein the ratio of water to the C1-C4 alcohol is 1:1 to 3:1 by volume.

7. The method of claim 1, wherein the acid is added at 1-10% by weight of the rutin-containing plant extract.

8. The method of claim 7, wherein the acid is added at 1-5% by weight of the rutin-containing plant extract.

9. The method of claim 8, wherein the acid is added at 2-4% by of the rutin-containing plant extract.

10. The method of claim 1, wherein the C1-C4 alcohol is methanol and the acid is ascorbic acid.

11. The method of claim 1, wherein the C1-C4 alcohol is n-butanol or propanol.

12. The method of claim 11, wherein the acid is ascorbic acid.

13. The method of claim 12, wherein the C1-C4 alcohol is n-butanol.

14. The method of claim 13, wherein the acid is added at 1-10% by weight of the rutin-containing plant extract.

15. The method of claim 14, wherein the acid is added at 1-5% by weight of the rutin-containing plant extract.

16. The method of claim 15, wherein the acid is added at 2-4% by weight of the rutin-containing plant extract.

17. The method of claim 13, wherein the ratio of water to the C1-C4 alcohol is 1:1 to 5:1 by volume.

18. The method of claim 13, wherein the ratio of water to the C1-C4 alcohol is 1:1 to 3:1 by volume.

\* \* \* \* \*